US012746297B2

(12) United States Patent
Chekmenev et al.

(10) Patent No.: US 12,746,297 B2
(45) Date of Patent: Sep. 29, 2026

(54) RADIOFREQUENCY AMPLIFICATION BY STIMULATED EMISSION OF RADIATION VIA PARAHYDROGEN INDUCED POLARIZATION

(71) Applicant: Wayne State University, Detroit, MI (US)

(72) Inventors: Eduard Y. Chekmenev, Troy, MI (US); Baptiste Joalland, Hamtramck, MI (US); Nuwandi M. Ariyasingha, Rochester Hills, MI (US)

(73) Assignee: Wayne State University, Detroit, MI (US)

( * ) Notice: Subject to any disclaimer, the term of this patent is extended or adjusted under 35 U.S.C. 154(b) by 1569 days.

(21) Appl. No.: 17/202,454

(22) Filed: Mar. 16, 2021

(65) Prior Publication Data

US 2021/0290781 A1 Sep. 23, 2021

Related U.S. Application Data

(60) Provisional application No. 62/990,787, filed on Mar. 17, 2020.

(51) Int. Cl.
*A61B 5/055* (2006.01)
*A61K 49/10* (2006.01)

(52) U.S. Cl.
CPC .................................... *A61K 49/10* (2013.01)

(58) Field of Classification Search
CPC ...................................................... A61K 49/10
See application file for complete search history.

(56) References Cited

U.S. PATENT DOCUMENTS

| | | | | |
|---|---|---|---|---|
| 9,702,946 B1 * | 7/2017 | Kovtunov | ............ | G01R 33/282 |
| 2015/0231357 A1 * | 8/2015 | Lu | ......................... | A61M 16/20<br>600/301 |
| 2019/0257907 A1 * | 8/2019 | Fain | ..................... | G01R 33/282 |

OTHER PUBLICATIONS

Lehmkuhl, S. (2019). Hyperpolarization with Parahydrogen in NMR (Publications No. RWTH-2019-02158) [Doctoral dissertation, RWTH Aachen University].*
Kovtunov et al. (Tomography 2016, 2(1), 49-55).*
Bouchard et al. (Science Jan. 25, 2008, 319 (5862), pp. 442-445).*
Goodson (Oct. 2016) Grant No. W81XWH-15-1-0272.*
Suefke, M., Lehmkuhl, S., Liebisch, A. et al., "Para-hydrogen raser delivers sub-millihertz resolution in nuclear magnetic resonance," Nature Phys, vol. 13, pp. 568-572, Jun. 2017.
Appelt, S., Kentner, A., Lehmkuhl, Sören, Bluemich, Bernhard, "From LASER physics to the para-hydrogen pumped RASER," Progress in Nuclear Magnetic Resonance Spectroscopy, vols. 114-115, pp. 1-32, May 28, 2019.
Suefke, M., Liebisch, A., Blümich, B. et al., "External high-quality-factor resonator tunes up nuclear magnetic resonance," Nature Phys, vol. 11, pp. 767-771, 2015.
Salnikov, Oleg G et al., "Parahydrogen-Induced Polarization of 1-13C-Acetates and 1-13C-Pyruvates Using Sidearm Hydrogenation of Vinyl, Allyl, and Propargyl Esters," J. Phys. Chem. C, Nanomaterials and interfaces, vol. 123, pp. 12827-12840, 2019.
Joalland, Baptiste, Schmidt, Andreas B., Kabir, Mohammad S. H., Chukanov, Nikita V., Kovtunov, Kirill V., Koptyug, Igor V., Hennig, Jürgen, Hövener, Jan-Bernd, Chekmenev, Eduard Y., "Pulse-Programmable Magnetic Field Sweeping of Parahydrogen-Induced Polarization by Side Arm Hydrogenation," Analytical Chemistry, vol. 92, No. 1, pp. 1340-1345, 2020.
Cavallari, E., Carrera, C., Boi, T., Aime, S., Reineri, F., "Effects of Magnetic Field Cycle on the Polarization Transfer from Parahydrogen to Heteronuclei through Long-Range J-Couplings," J Phys Chem B., vol. 119, No. 31, pp. 10035-10041 Aug. 6, 2015.
Bhattacharya, P., Harris, K., Lin, AP, Mansson, M., Norton, VA, Perman, WH, Weitekamp, DP, Ross, BD, "Ultra-fast three dimensional imaging of hyperpolarized 13C in vivo," MAGMA, vol. 18, No. 5, pp. 245-256, Nov. 2005.
Golman, K., Axelsson, O., Jóhannesson, H., Månsson, S., Olofsson, C., Petersson, JS, "Parahydrogen-induced polarization in imaging: subsecond (13)C angiography," Magn Reson Med., vol. 46, No. 1, pp. 1-5, Jul. 2001.
Waddell, Kevin W.; Coffey, Aaron M.; Chekmenev, Eduard Y., T1—In Situ Detection of PHIP at 48 mT: Demonstration Using a Centrally Controlled Polarizer,' J. Am. Chem. Soc., vol. 133, No. 1, pp. 97-101, Dec. 9, 2010.
Cai, C., Coffey, AM, Shchepin, RV, Chekmenev, EY, Waddell, KW, "Efficient Transformation of Parahydrogen Spin Order into Heteronuclear Magnetization," J Phys Chem B., vol. 117, No. 5, pp. 1219-1224, Dec. 7, 2012.
Goldman, Maurice, Jóhannesson, Haukur, "Conversion of a proton pair para order into 13C Polarization by rf irradiation, for use in MRI," Comptes Rendus Physique, vol. 6, Nos. 4-5, pp. 575-581, 2005.
Goldman, Maurice, Jóhannesson, Haukur, Axelsson, Oskar, Karlsson, Magnus,, "Design and implementation of 13C hyper polarization from para-hydrogen, for new MRI contrast agents," Comptes Rendus Chimie, vol. 9, Nos. 3-4, pp. 357-363, 2006.
Reineri F, Boi T, Aime S., "ParaHydrogen Induced Polarization of 13C carboxylate resonance in acetate and pyruvate," Nat Commun, vol. 6, No. 1, pp. 5858-5858, Jan. 5, 2015.
Shchepin, RV, Barskiy, DA, Coffey, AM, Manzanera, Esteve IV, Chekmenev, EY, "Efficient Synthesis of Molecular Precursors for Para-Hydrogen-Induced Polarization of Ethyl Acetate-1-(13) C and Beyond," Angewandte Chemie (International ed. in English)., vol. 55, No. 20, pp. 6071-6074, May 10, 2016.

(Continued)

*Primary Examiner* — Michael G. Hartley
*Assistant Examiner* — Melissa J Perreira
(74) *Attorney, Agent, or Firm* — Fishman Stewart PLLC

(57) ABSTRACT

A RASER-inducing contrast agent for magnetic resonance (MR) modalities that includes a parahydrogen addition to unsaturated molecular precursor that renders radio amplification by stimulated emission of radiation (RASER) of protons and other nuclear spins.

5 Claims, 18 Drawing Sheets

(56) References Cited

OTHER PUBLICATIONS

Pravdivtsev, AN, Sönnichsen, FD, Hövener, JB, "Continuous Radio Amplification by Stimulated Emission of Radiation using Parahydrogen Induced Polarization (PHIP-RASER) at 14 Tesla," Chemphyschem, vol. 21, No. 7, pp. 667-672, Apr. 2, 2020.

* cited by examiner partial RASER

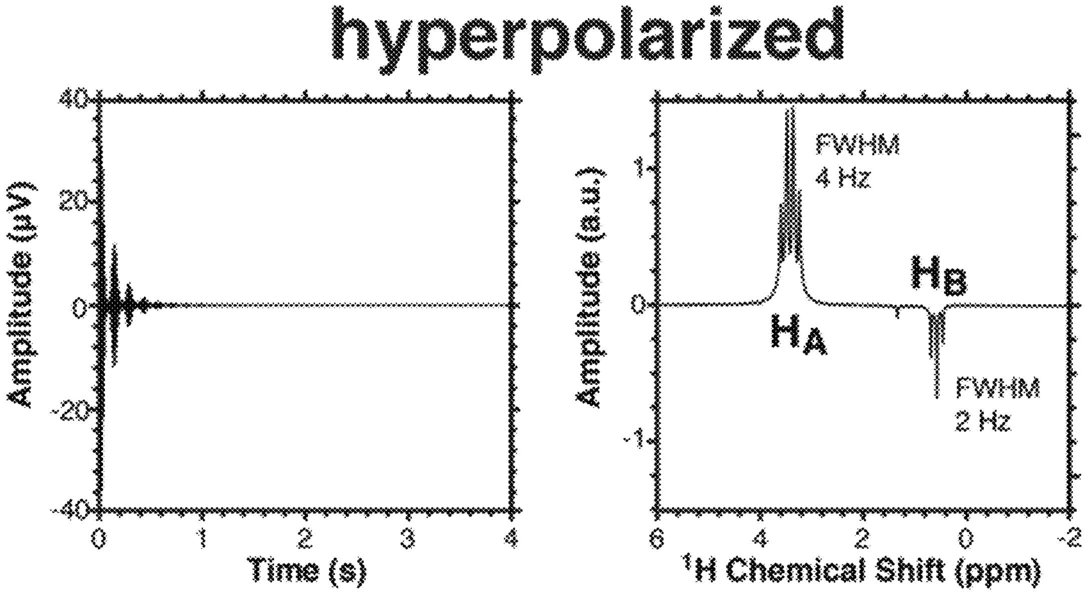
FIG. 3F
FIG. 3G
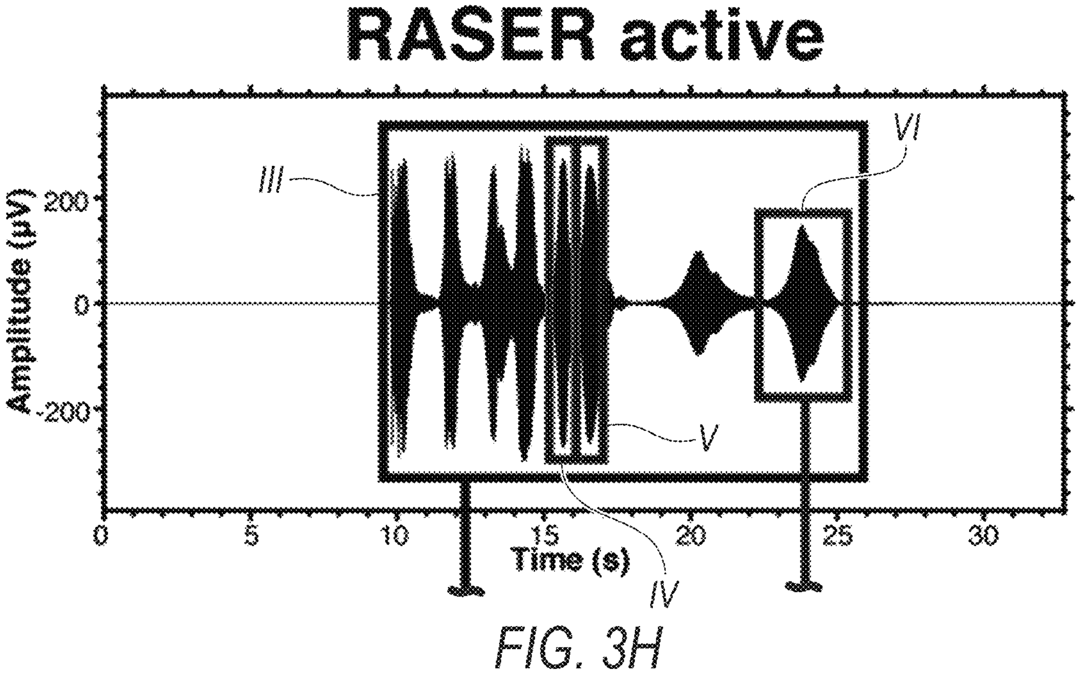
FIG. 3H hyperpolarized

RASER active partial RASER # partial RASER hyperpolarized

HP EA (~0.04 M)

ALTADENA RASER active

RADIOFREQUENCY AMPLIFICATION BY STIMULATED EMISSION OF RADIATION VIA PARAHYDROGEN INDUCED POLARIZATION

CROSS-REFERENCE TO RELATED APPLICATIONS

This application claims the benefit of U.S. Application Ser. No. 62/990,787 filed on Mar. 17, 2020, the contents of which are incorporated herein in their entirety.

GOVERNMENT LICENSE RIGHTS

This invention was made with government support under the following: contract no. R21 CA220137 awarded by the National Institutes of Health; contract no. CHE-1836308 and CHE-1904780 awarded by the National Science Foundation; and contract no. W81XWH-15-1-0271 awarded by the Department of Defense. The government has certain rights in the invention.

TECHNICAL FIELD

This disclosure relates generally to magnetic resonance (MR) technology and contrast agents used in MR technologies

BACKGROUND

There have been experimental observations of radio amplification by stimulated emission of radiation (RASER) of protons. Unlike lasers and masers, which employ self-organizing systems emitting coherent optical- and micro-waves, RASER is induced by continuous coherent oscillation of radio waves at much lower frequencies through the coupling between nuclear spin magnetization and an LC resonance circuit. Because the magnetization, i.e., the product of the concentration of nuclear spins and their nuclear spin polarization (P) or the degree of the spin alignment with the static magnetic field of the NMR magnet, is high, RASER-based nuclear magnetic resonance (NMR) spectroscopy is difficult to achieve using thermal nuclear spin polarization. Hyperpolarization techniques allow for enhancing the nuclear spin polarization by several orders of magnitude up to unity. Further, Signal Amplification by Reversible Exchange (SABRE) can provide a highly magnetized sample in RASER demonstrations. SABRE generally relies on the simultaneous exchange between parahydrogen ($p\text{-}H_2$, the source of hyperpolarization) and a substrate on a metal complex. With SABRE, the spontaneous polarization of proton spins is generally efficient in the magnetic field range of approximately 1 to 10 mT. NMR detection at magnetic fields of several milli-Tesla with corresponding resonance frequencies in the range of 41-512 kHz have been employed. It is noted that SABRE has been employed because it generally allows for continuously regenerating the proton polarization via the sustained delivery of $p\text{-}H_2$ gas to the sample placed inside the NMR detector.

RASER activity is generally initiated when the radiation damping rate 1/τRD satisfies the following condition: $1/\tau_{RD}>1/T_2^*$ (Equation 1). $1/T_2^*$ defines the modified spin-spin relaxation rate and $1/\tau_{RD}$ the radiation damping rate, which is given by: $1/\tau_{RD}=-(\mu_0/2)*\eta*Q*\gamma*M_0=-(\mu_0/4)*\eta*Q*\gamma2*h*n_s*$ (Equation 2), where $\mu_0$, $\eta$, Q, $\gamma$, h, and $n_S$ are defined as the vacuum permeability, the filling factor of the resonator, the quality factor of the resonator, the gyromagnetic ratio, Planck's constant, and the spin number density, respectively.

The initial magnetization is given as M0=(1/2)*h*γ*nS*P, where P is the degree of spin polarization. Note that if P>0, the rate 1/τRD is negative and the associated line is additionally broadened by radiation damping with a total damping rate $\kappa_{tot}=(1/T_2^*-1/\tau_{RD})>1/T_2^*$. If P<0, which corresponds to a population inversion, $1/\tau_{RD}$ is positive and the line is narrowed due to the decreased total damping rate $\kappa_{tot}<1/T_2^*$. RASER activity starts if $\kappa_{tot}<0$, as described by Equation (1). To fulfill this condition for proton spins at low frequencies, high-quality (e.g., Q~300) resonators have been employed, which reduce the RASER threshold requirements for polarization and concentration.

In addition to employing high-quality resonators to achieve relevant magnetization, others have employed cryogenic equipment to boost quality factor of the RF coil to help the establish RASER.

While techniques described above have shown the feasibility of employing RASER in the field of NMR spectroscopy, capitalizing on the benefits of RASER in the field of nuclear magnetic resonance imaging (MRI) poses its own unique challenges. For example, commercial MRI equipment often does not include the highly-specialized RF coils employed in NMR spectroscopy. Further, often commercial MRI equipment does not include specialized cryogenic equipment to boost the quality factor of the RF coil to help establish RASER, as done in some NMR spectroscopy implementations.

Accordingly, there is a need to address challenges and shortcomings so that RASER techniques may be effectively employed in a variety of MRI settings.

BRIEF DESCRIPTION OF THE DRAWINGS

FIG. 3A-3L illustrates an exemplary $^1H$ NMR spectroscopy of solution-phase PHIP of 0.4 M HP ethyl acetate (EA) probed at 1.4 T, where FIG. 3A illustrates an exemplary ALTADENA RASER signal recorded without implementation of an RF pulse after hydrogenation in the Earth's magnetic field;

FIG. 3B illustrates an exemplary Fourier spectra of the region outlined by box I of FIG. 3A;

FIG. 3C illustrates an exemplary Fourier spectra of the region outlined by box II of FIG. 3A;

FIG. 3D illustrates an exemplary Partial ALTADENA RASER signal obtained with a ~3° RF pulse;

FIG. 3E illustrates an exemplary Fourier spectrum obtained with an ~3° RF pulse;

FIG. 3F illustrates an exemplary canonical ALTADENA (non-RASER) FID after further polarization decay;

FIG. 3G illustrates an exemplary Fourier spectrum recorded after further polarization decay;

FIG. 3H illustrates an exemplary PASADENA RASER signal recorded without an RF pulse after hydrogenation at 1.4 T;

FIG. 3I illustrates an exemplary Fourier spectra of the region outlined by box III of FIG. 3H;

FIG. 3J illustrates an exemplary Fourier spectra of the region outlined by box IV of FIG. 3H;

FIG. 3K illustrates an exemplary Fourier spectra of the region outlined by box V of FIG. 3H;

FIG. 3L illustrates an exemplary Fourier spectra of the region outlined by box VI of FIG. 3H;

FIG. 4A illustrates an exemplary ALTADENA RASER signal recorded without an RF pulse after hydrogenation in the Earth's magnetic field;

FIG. 4N illustrates an exemplary Fourier spectrum acquired with an ~3° RF pulse after further polarization decay (~30 s);

DETAILED DESCRIPTION

Parahydrogen-Induced Polarization (PHIP) is employed to, in part, quickly create a batch of proton magnetization that can be inhaled or injected into a living subject (including human) and employed as a contrast agent for enhanced Magnetic Resonance Imaging (MRI) scan. At least one practical utility is the use of stimulated emission produced by an injected or inhaled bolus of parahydrogen-hyperpolarized contrast agent.

Figure 1:
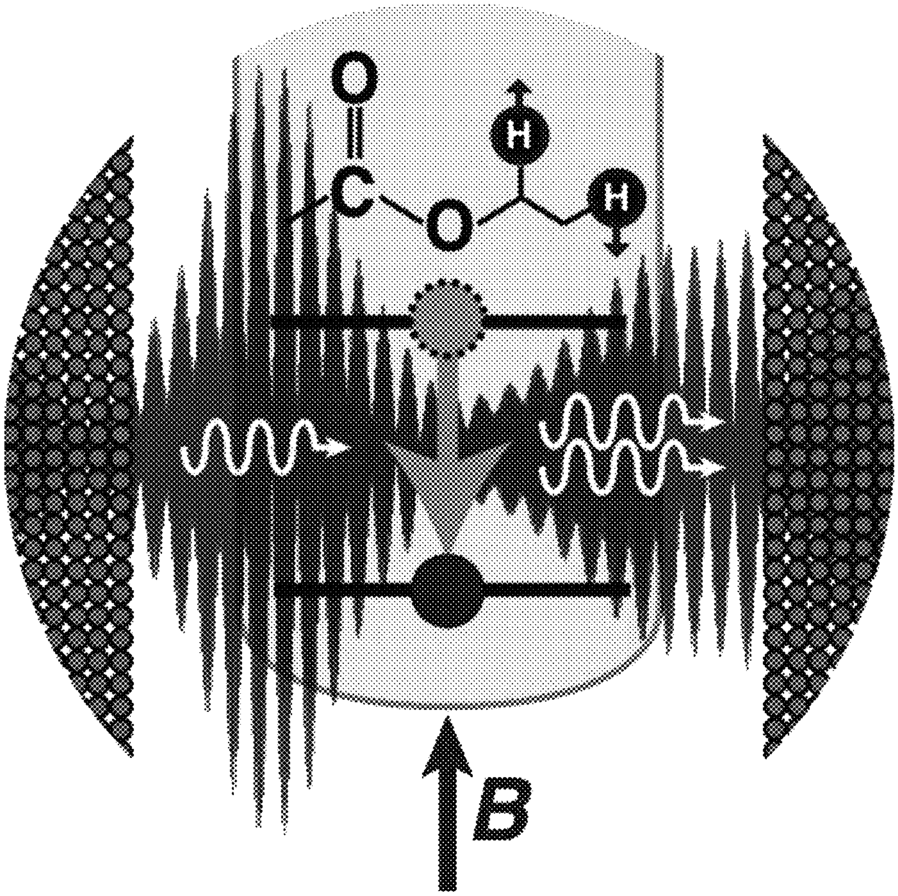
FIG. 1 illustrates a schematic of radio amplification by stimulated emission of radiation (RASER) of parahydrogen-derived protons from the reaction of pairwise parahydrogen addition.

Referring now to the figures, FIG. 1 illustrates a schematic of radio amplification by stimulated emission of radiation (RASER) of parahydrogen-derived protons from the reaction of pairwise parahydrogen addition. Radio amplification by stimulated emission of radiation (RASER) condition is the result of the interaction between the injected or inhaled bolus of hyperpolarized contrast agent and the radio-frequency RF coil resonating at the Larmor frequency of the corresponding nucleus (proton employed here) in the MRI/NMR homogeneous magnet.

Unlike a conventional hyperpolarized state (where the nuclear spin polarization significantly exceeds that of equilibrium nuclear spin polarization), the RASER-active hyperpolarized state generally needs to possess both sufficiently high concentration and magnetization in order to start RASER: interaction with the RF coil leading to the stimulated emission (see. e.g., FIG. 1). Moreover, the quality factor of the RF coil generally needs to be sufficiently large in order sustain RASER condition.

Figure 2A:
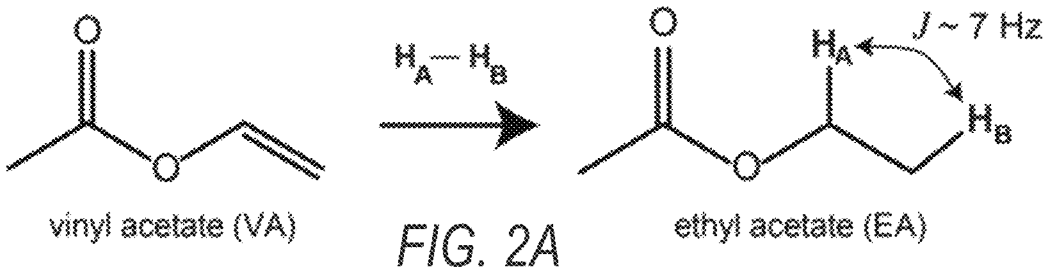
FIGS. 2A-2B illustrate exemplary reaction schemes for the $p\text{-}H_2$ pairwise addition to vinyl acetate (VA) yielding to ethyl acetate (EA) and to 2-2-hydroxyethyl acrylate (HEA) yielding to 2-hydroxyethyl propionate (HEP), respectively.
Figure 2B:
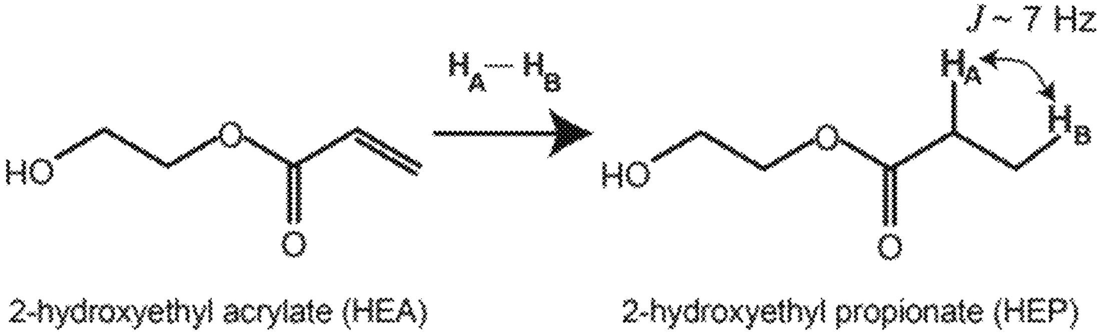
Figure 2C:
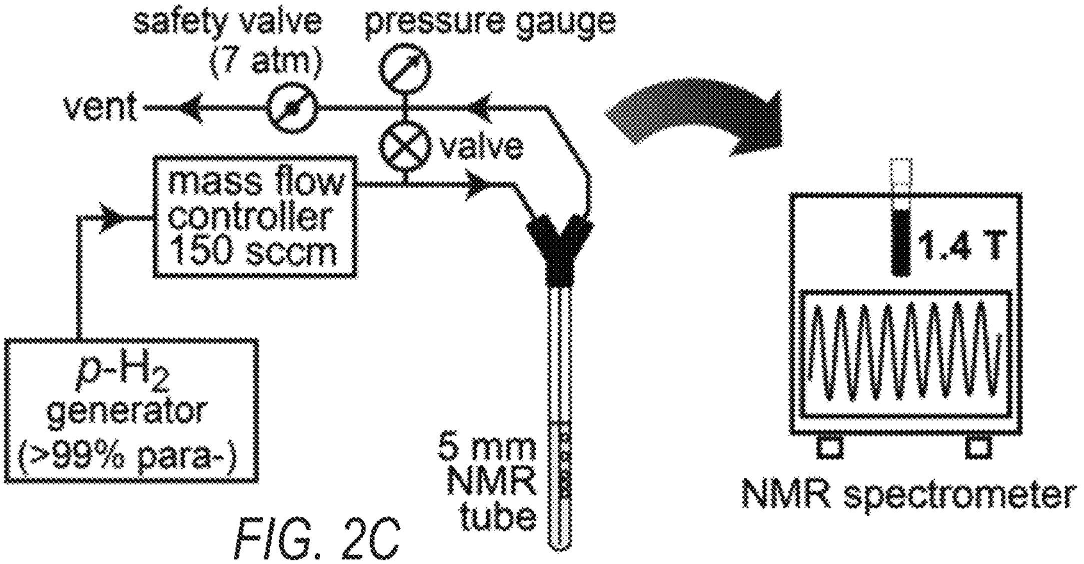
FIG. 2C illustrates an exemplary schematic of an experimental setup.

Herein, it is shown that a commercial, high-field MR system with standard inductive detection (i.e., without specialized, high-Q resonators) can readily detect RASER when combined with a parahydrogen-induced polarization (PHIP) technique. A 1.4 T (61.7 MHz) bench-top NMR spectrometer (SpinSolve Carbon 60, Magritek, New Zealand) with Q=68 to induce RASER of protons in hyperpolarized (HP) ethyl acetate (EA) and 2-hydroxyethylpropionate (HEP) was employed to show results. These HP compounds were formed through the pairwise addition of p-$H_2$ onto the unsaturated C═C chemical bonds of the substrates vinyl acetate (VA) and 2-hydroxyethyl acrylate (HEA), respectively (see, e.g., FIGS. 2A and 2B). The symmetry breaking of the nascent p-$H_2$-derived protons allows for the hyperpolarization to become observable. The solutions were prepared with ~0.4 M of substrates and 4 mM of catalyst (Bicyclo[2.2.1]hepta-2,5-diene) [1,4-bis(diphenylphosphino) butane]rhodium (I) tetrafluoroborate (Sigma-Aldrich, P/N 341126-100 MG) in $CD_3OD$. Nearly 100% p-$H_2$ was employed using a home-built cryogenic generator. At 75° C. and 100 psi, the substrates were fully converted into their respective HP products via bubbling p-$H_2$ for 15 second with a 150 sccm flow rate controlled by a mass-flow controller, as described previously (see, e.g., FIG. 2C). The polarization of HA and HB was estimated to be between 10% and 20% and their $T_1$ relaxation times was measured to be ~16-25 seconds.

Figure 2D:
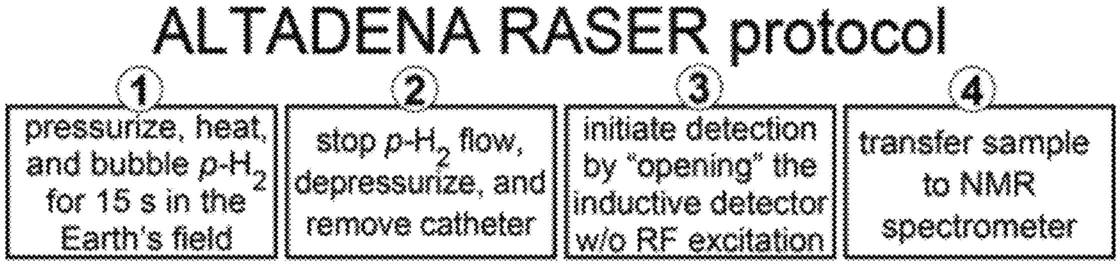
FIG. 2D illustrates an exemplary ALTADENA protocol used to evidence parahydrogen-induced RASER activity.
Figure 2E:
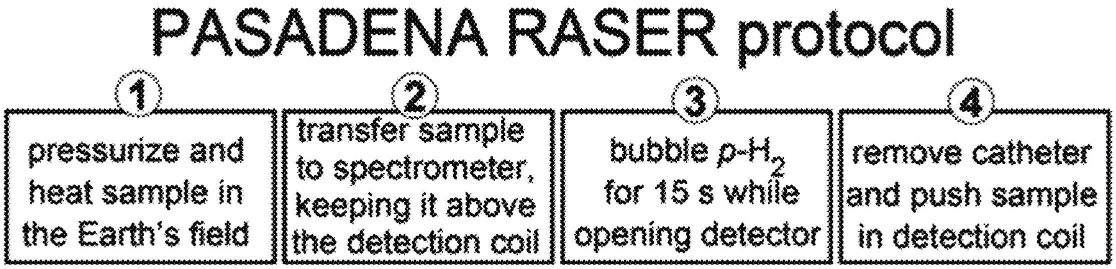
FIG. 2E illustrates an exemplary PASADENA protocol used to evidence parahydrogen-induced RASER activity.

Two exemplary experimental protocols were followed. The first exemplary protocol corresponds to the exemplary ALTADENA condition. In this case, the samples were hydrogenated in the Earth's magnetic field (~50 μT). The p-$H_2$ flow was then interrupted, the sample depressurized, the catheter removed, the "pulse-and-acquire sequence" initiated, and the sample inserted in the NMR spectrometer (see e.g., FIG. 2D). So that the sample did not experience any RF excitation, or at least to substantially reduce any such RF excitation, the sample was inserted several seconds after an RF pulse sequence with a flip angle lower than 0.01° was initiated. As such, the RF pulse was applied before the sample insertion, thus the detected signal is not due to stimulation by an RF pulse. The detector channel was opened for up to 32 seconds. The second protocol corresponds to the exemplary PASADENA condition, in which the hydrogenation reaction was performed at 1.4 T, i.e., inside the spectrometer. During the hydrogenation reaction, the sample was positioned approximately 4-5 cm above the RF coil so the catheter could be removed without interfering with the signal detection, which was initiated before the hydrogenation reaction was completed. Once the reaction was completed and the catheter removed, the sample was pushed inside the RF coil (see. e.g., FIG. 1E). Since the pulse sequence was started before the sample insertion in the active detection volume, the detected signal is not due to stimulation by an RF pulse.

Figure 3A:
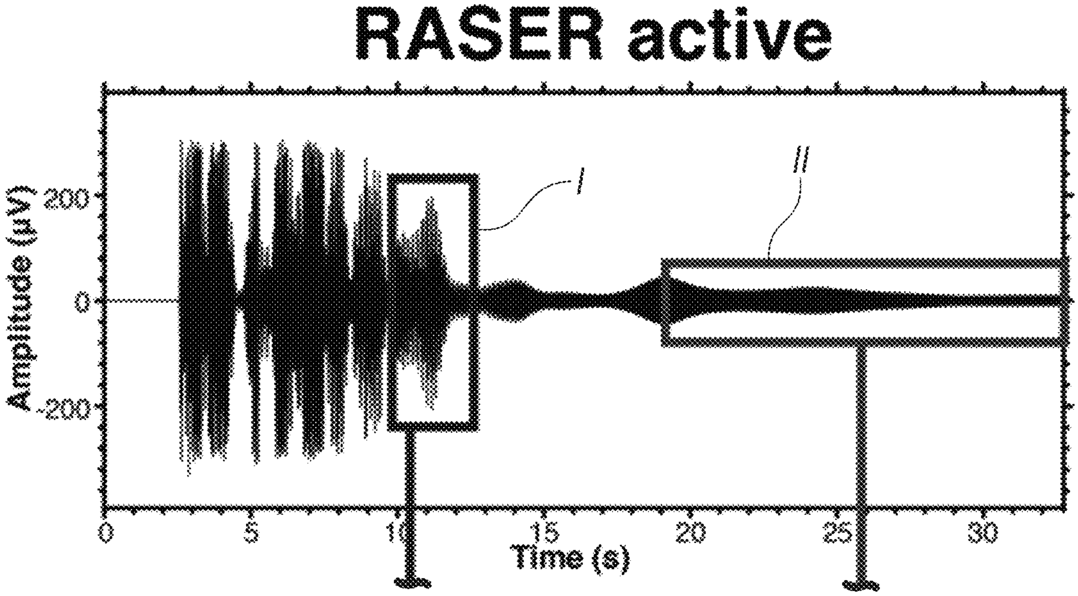

Results obtained for hyperpolarized EA and HEP as illustrated in Figure sets of 3 and 4, respectively, are shown. For both the exemplary ALTADENA and exemplary PASADENA experiments, the NMR signal exhibits the characteristic features of RASER activity: that is, signal persistence for significantly longer periods of time than $T_2$* of ~0.6 s. The Fourier transformed spectra of selected regions with defined duration of the exemplary RASER active signals (e.g., FIGS. 3B-C for ALTADENA and FIG. 3I-L for PASADENA), illustrate the enhanced spectral resolution due to RASER activity with sharp peaks with FWHM<0.2 Hz, where the resolution of the spectrometer is ~0.5 Hz after full shimming and ~2 Hz in case of conventional HP experiments. After these exemplary RASER active signals were recorded, additional NMR spectra were acquired using an ~3.3° excitation RF pulse. The first of those spectra show partially RASER active NMR lines (see, e.g., FIG. 3E in case of ALTADENA and FIG. 4L in case of PASADENA), while the subsequent acquisitions correspond to normal, hyperpolarized ALTADENA (see, e.g., FIGS. 3G and 4G) and PASADENA (e.g., FIGS. 3N and 4N) spectra.

Figure 3B:
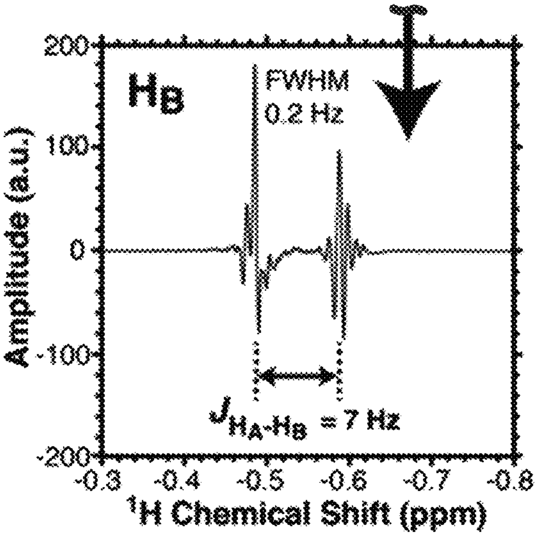
Figure 3C:
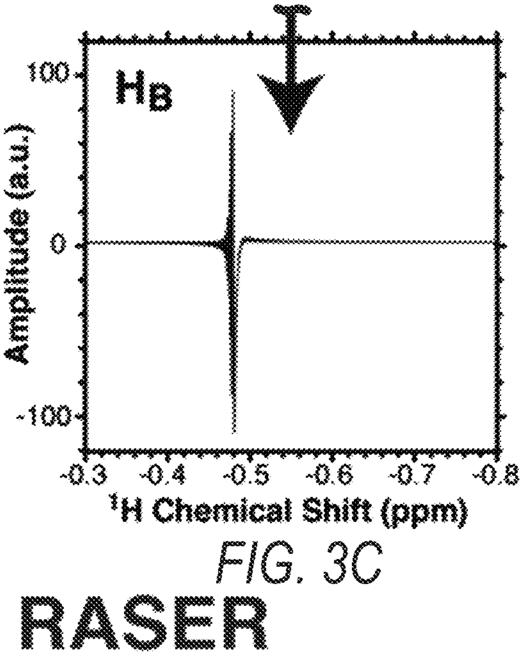
Figure 3D:
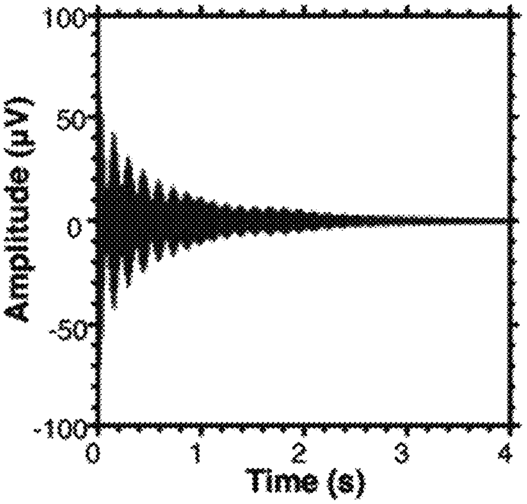
Figure 3E:
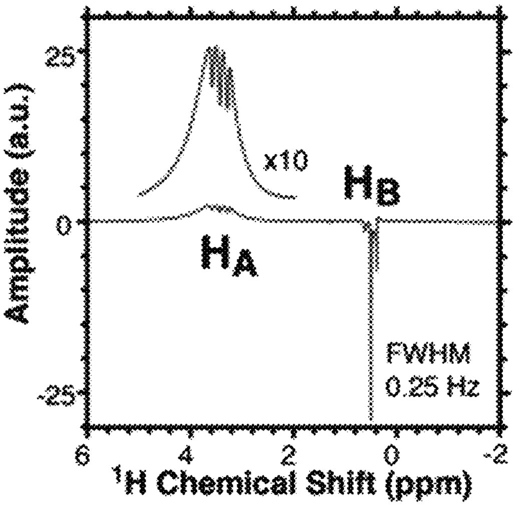
Figures 3I, 3J, 3K, 3L:
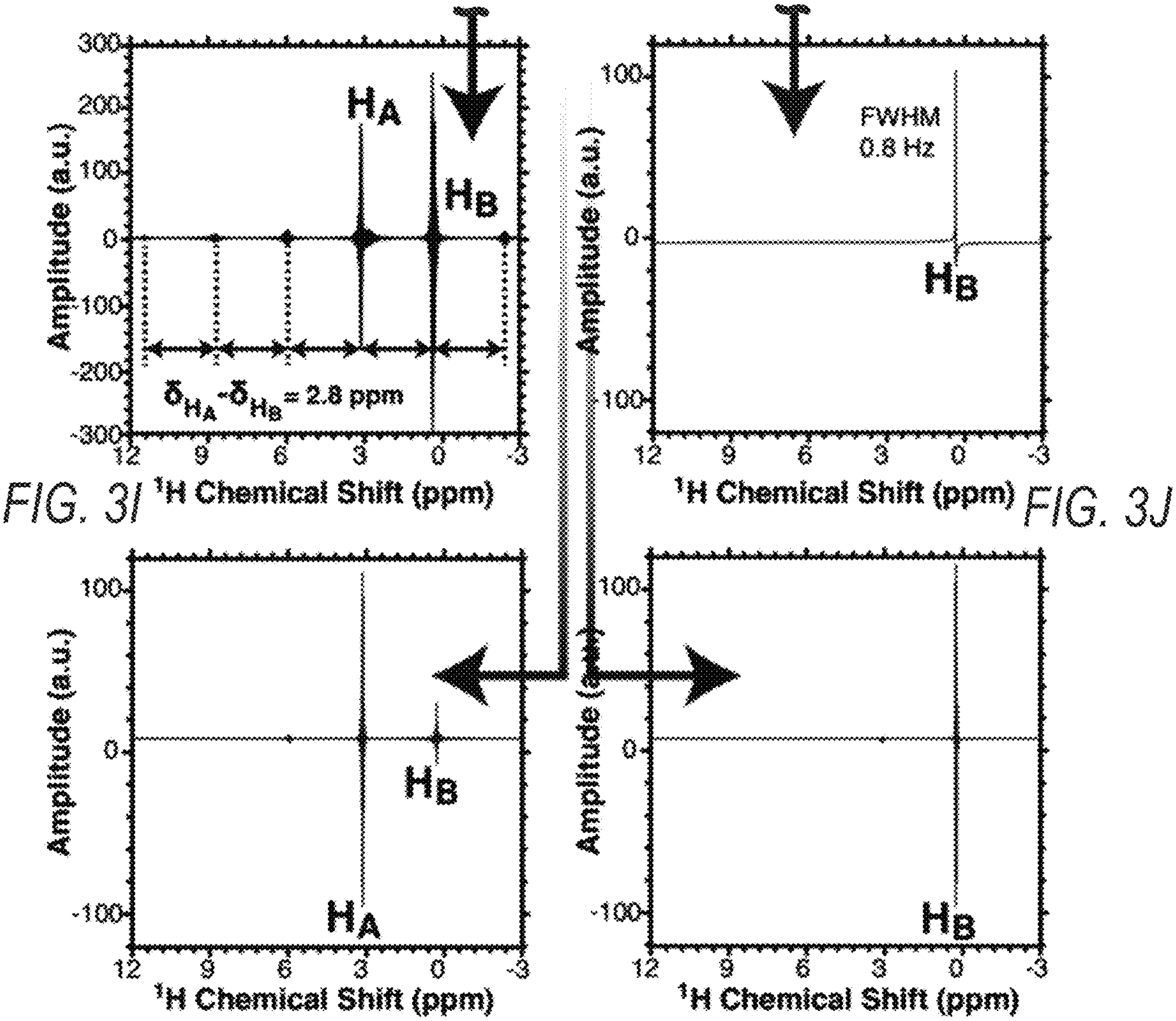
Figure 3M:
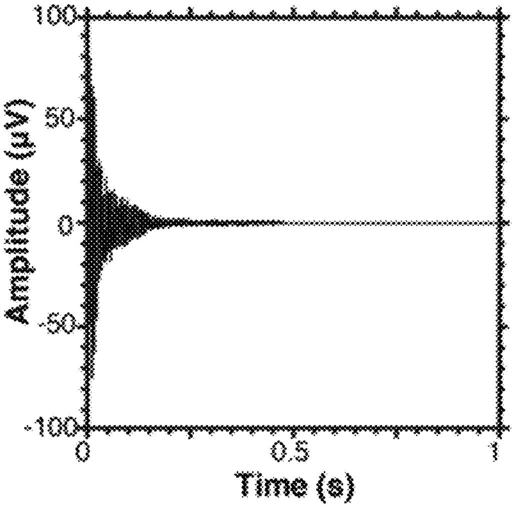
FIG. 3M illustrates an exemplary canonical PASADENA (non-RASER) FID acquired with an ~3° RF pulse after further polarization decay (~30 s)
Figure 3N:
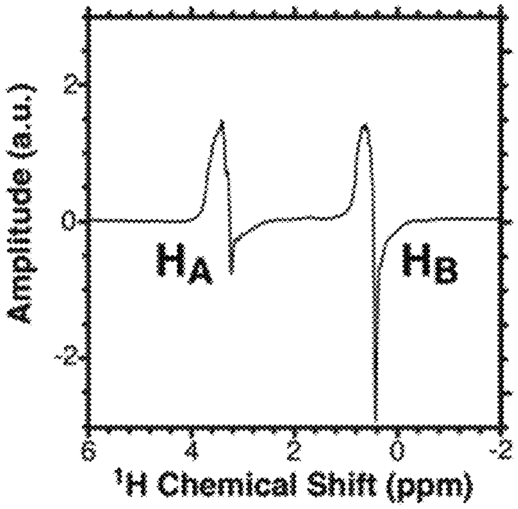
FIG. 3N illustrates an exemplary Fourier spectrum acquired with an ~3° RF pulse after further polarization decay (~30 s)
Figure 4A:
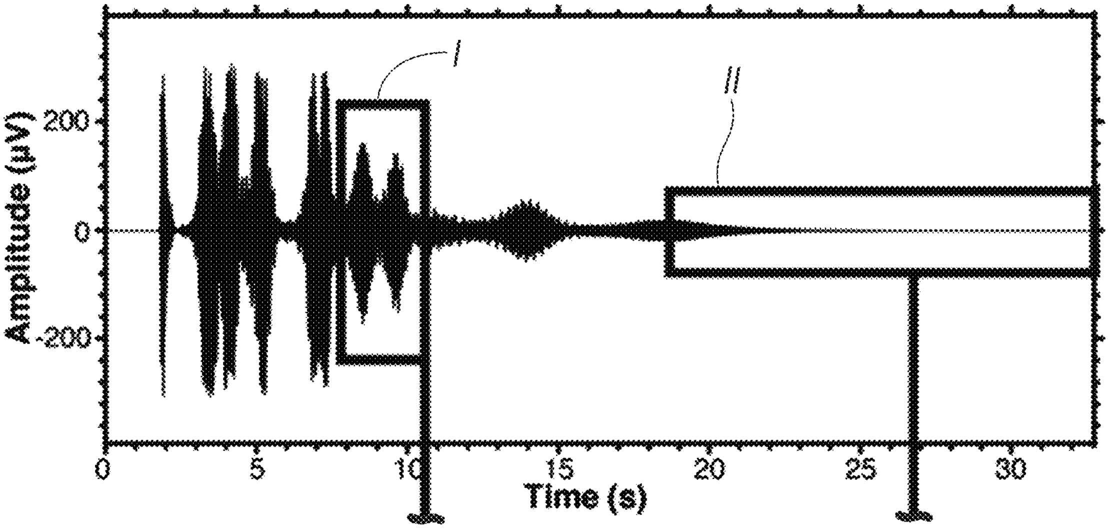
FIG. 4A-N illustrate an exemplary $^{1}H$ NMR spectroscopy of solution-phase PHIP of 0.4 M HP 2-hydroxyethyl propionate (HEP) probed at 1.4 T, where
Figure 4B:
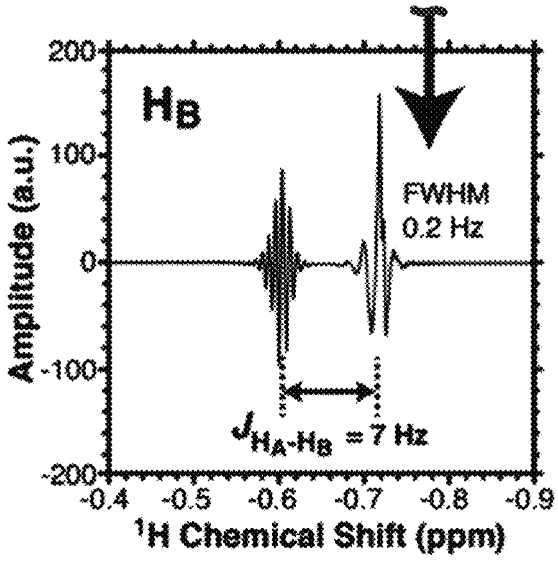
FIG. 4B illustrates an exemplary Fourier spectra of the region outlined by box I of FIG. 4A.
Figure 4C:
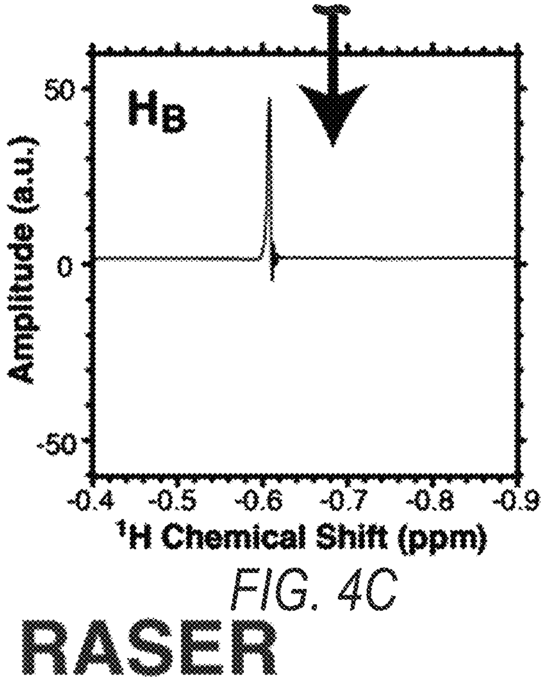
FIG. 4C illustrates an exemplary Fourier spectra of the region outlined by box I of FIG. 4A.
Figure 4D:
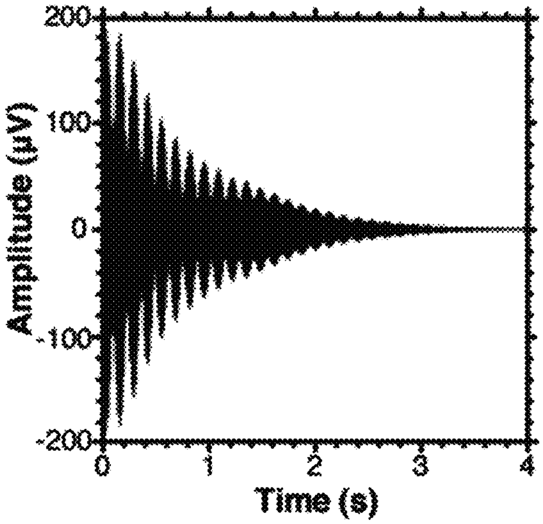
FIG. 4D illustrates an exemplary Partial ALTADENA RASER signal acquired using an ~3° RF pulse.

With ALTADENA, the exemplary Fourier spectra of the time slices of the RASER active signals (displayed, e.g., in FIGS. 3A and 4A) show a doublet (see, e.g., FIGS. 3B and 4B). These two RASER resonances can be attributed to lines in the PHIP spectra depicted in FIGS. 3G and 4G respectively. In particular, each of the three triplet lines corresponding to proton HB are population inverted (have negative sign) and its two most intense lines are RASER active. The doublet is separated by splitting corresponding to the spin-spin coupling JHA-HB of 7.0 Hz between proton HA and HB in EA and HEP (see, e.g., FIGS. 3B and 4*b* respectively). While the HP state decays, the number of RASER active lines changes, for example from two RASER active lines in FIGS. 3B and 4B to one single line in, for example, FIGS. 3C and 4C correspondingly. This may be explained by different transverse relaxation rates and multiplicities of each RASER line. For instance, at low polarization, only one line with the highest amplitude in the NMR spectrum and with the smallest line-width overcomes the RASER threshold and is RASER active.

Figure 4E:
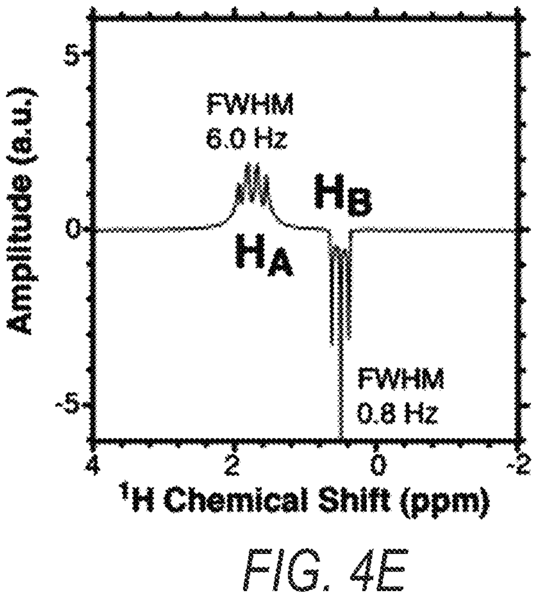
FIG. 4E illustrates an exemplary Fourier spectrum acquired using an ~3° RF pulse.
Figure 4F:
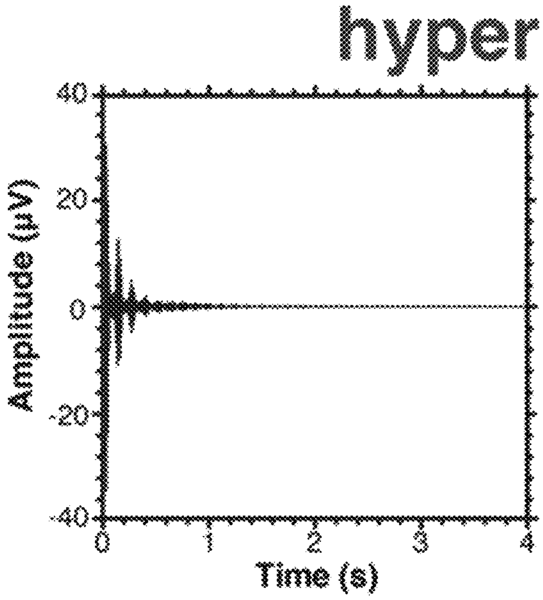
FIG. 4F illustrates an exemplary Canonical ALTADENA (non-RASER) FID recorded after further polarization decay (~30 s)
Figure 4G:
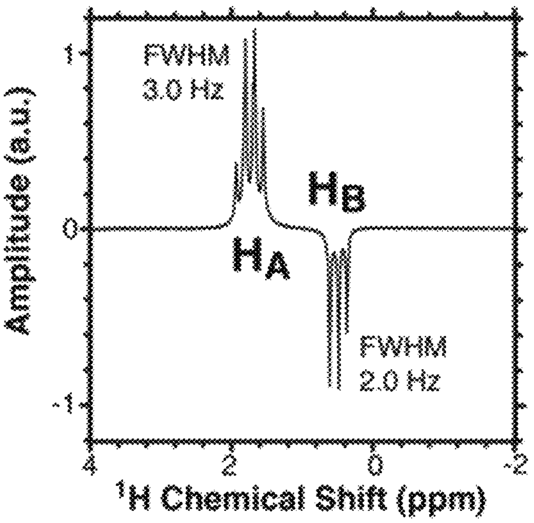
FIG. 4G illustrates an exemplary Fourier spectrum recorded after further polarization decay (~30 s)

Exemplary ALTADENA-hyperpolarized RASER spectra from Figure sets of 3 and 4 differ from the corresponding PHIP spectra in FIGS. 3G and 4G. The latter feature the HP resonances of HA and HB with the lines of the quartet and the triplet spectrum of opposite signs. These quartet and triplet are separated by ~2.8 ppm (~174 Hz) for EA and ~1.2 ppm (~74 Hz) for HEP. The linewidth of the quartet FWHM of ~4 Hz in FIG. 3G is broader compared to the linewidth of each of the triplet lines with FWHM of ~2 Hz. This is more pronounced in FIG. 3E, where the difference in linewidth is more than one order of magnitude. The same trend is observed in FIGS. 4E and 4G. The reason for this is the sign and the magnitude of the HP state, which introduce a broadening with $\kappa_{tot}>1/T_2^*$ for the quartet lines and a narrowing with $\kappa_{tot}<1/T_2^*$ of the triplet lines. For the exemplary RASER lines in FIGS. 3B and 4B, $\kappa_{tot}$ is negative, and the linewidth in principal is only limited by the finite measurement time and ultimately by the Cramér-Rao condition. It is concluded that the RASER spectra of VA and HEP hyperpolarized by ALTADENA allow the J-coupling constant JHA-HB to be determined with enhanced precision but the chemical shift difference between HA and HB is not measurable in this RASER experiment.

Figure 4H:
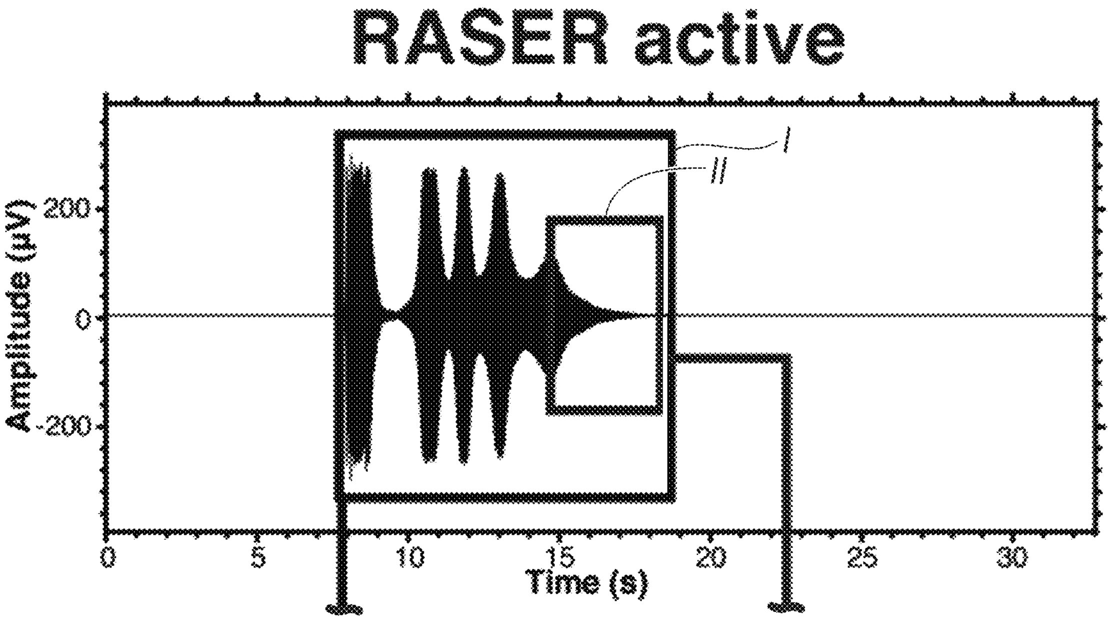
FIG. 4H illustrates an exemplary PASADENA RASER signal recorded without an RF pulse after hydrogenation at 1.4 T.
Figure 4I:
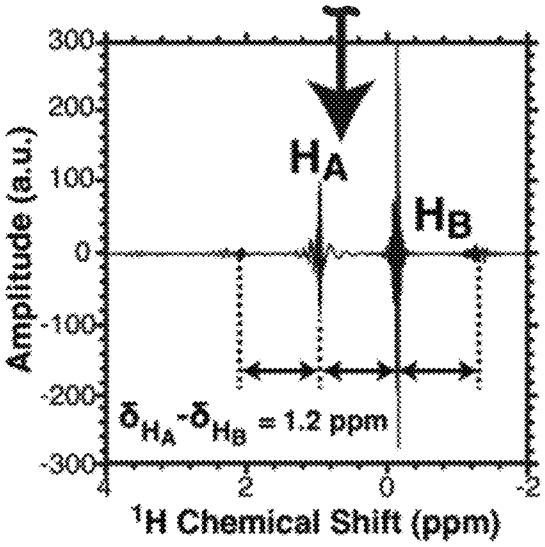
FIG. 4I illustrates an exemplary Fourier spectra of the regions outlined by box I of FIG. 4H.
Figure 4J:
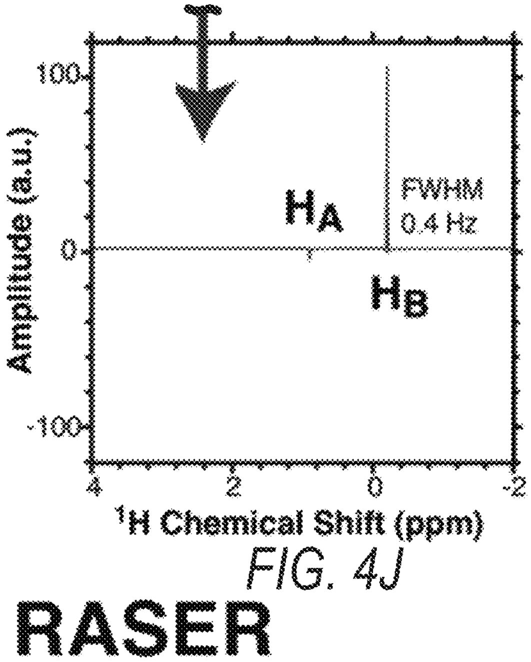
FIG. 4J illustrates an exemplary Fourier spectra of the regions outlined by box II of FIG. 4H.
Figure 4K:
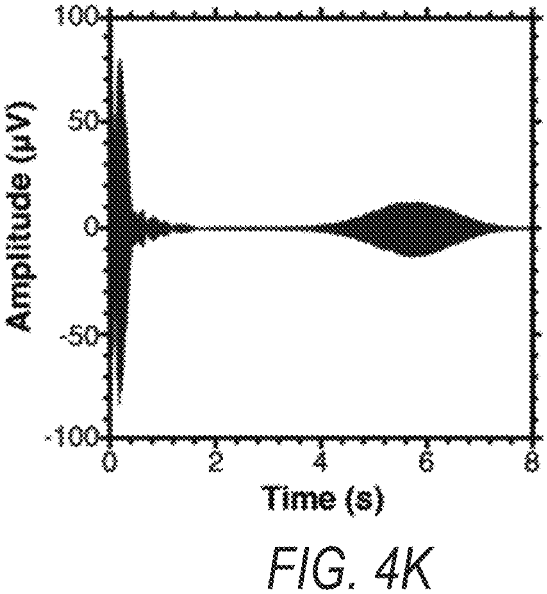
FIG. 4K illustrates an exemplary Partial PASADENA RASER signal acquired using an ~3° RF pulse.
Figure 4L:
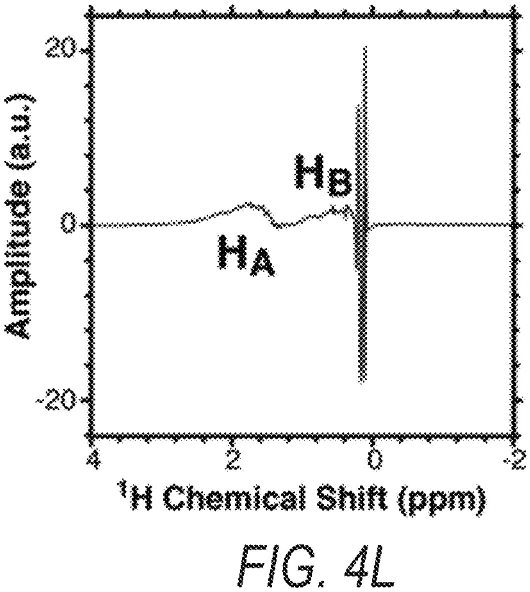
FIG. 4L illustrates an exemplary Fourier spectrum acquired using an ~3° RF pulse.
Figure 4M:
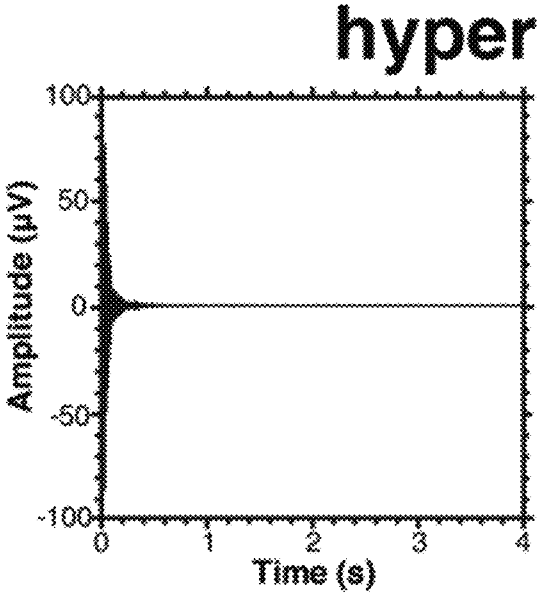
FIG. 4M illustrates an exemplary Canonical PASADENA (non-RASER) FID and acquired with an ~3° RF pulse after further polarization decay (~30 s)
Figure 4N:
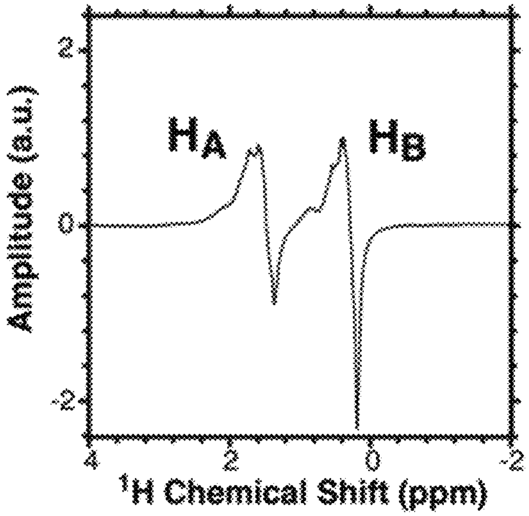

The analysis of the exemplary RASER active signals in the PASADENA case (e.g., FIGS. 3H and 4H) renders other observations in addition to the line narrowing. For example, the exemplary Fourier spectra of the RASER active signals (see, e.g., FIGS. 3I and 4I) exhibit two generally large central RASER lines separated by the chemical shift difference SHA-SHB between the HA and HB protons, i.e., $\delta_{HA}-\delta_{HB}$=2.8 ppm (~174 Hz) for EA and 1.2 ppm (~74 Hz) for HEP. The two central lines are accompanied by evenly spaced small sidebands, and the distance between two consecutive lines is $\delta_{HA}-\delta_{HB}$. This can be explained by the non-linear interaction between different RASER active modes (here two), leading to a frequency comb like spectrum. There is also an even frequency comb-like spectra in the case of the ALTADENA pumped RASER, where the two central modes and all sidebands are spaced by JHA-HB. Moreover, the resonance frequencies of the RASER active protons (see, e.g., FIGS. 3B, 3C, 4B, and 4C) are sometimes shifted by about 1 ppm when compared with the partial RASER and hyperpolarized ones. This shifting may be due to the magnetic field fluctuations induced by RASER.

A series of additional experiments performed demonstrate further that the experimental conditions for observing RASER through PHIP reactions are generally not stringent.

Figure 5A:
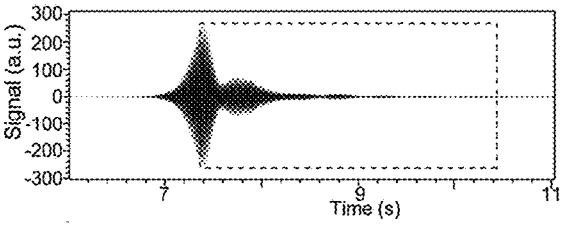
FIG. 5A illustrates an exemplary $^{1}H$ NMR spectroscopy of solution-phase PHIP of 40 mM HP ethyl acetate (EA) probed at 1.4 T represented in an ALTADENA RASER active signal.
Figure 5B:
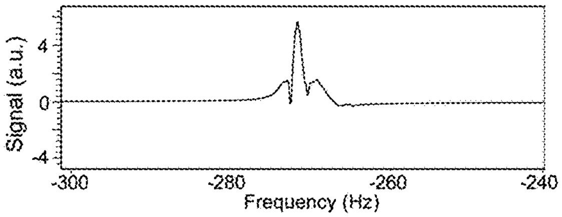
FIG. 5B illustrates an exemplary $^{1}H$ NMR spectroscopy of solution-phase PHIP of 40 mM HP ethyl acetate (EA) probed at 1.4 T represented Fourier spectrum.

RASER bursts can indeed be observed with more dilute samples, as illustrated by the exemplary NMR signal shown in FIG. 5 and obtained with a 40 mM VA solution. This indicates that PHIP RASER occurs at relatively low concentrations of HP substrate suitable for potential biomedical application. For example, gas concentration of ideal gas at 1 atm is >40 mM. If the lungs of a subject are filled with an HP gas it may, therefore, be possible to create a RASER condition and perform a RASER MRI scan on a subject having HP gas in said subject's lungs.

Figure 6A:
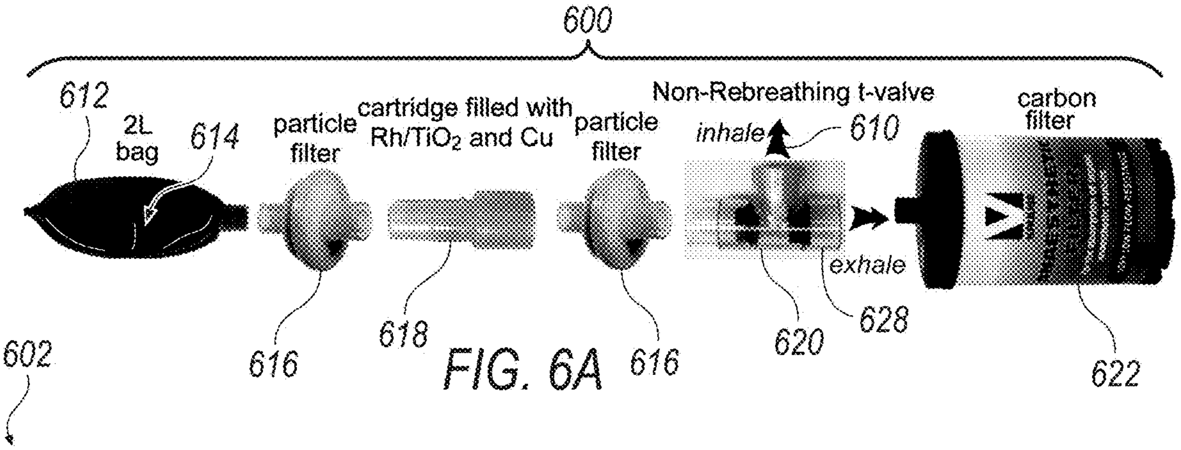
FIG. 6A illustrates an exploded view of an exemplary apparatus for the creation and administration of a RASER-enhanced hyperpolarized contrast agent.
Figure 6B:
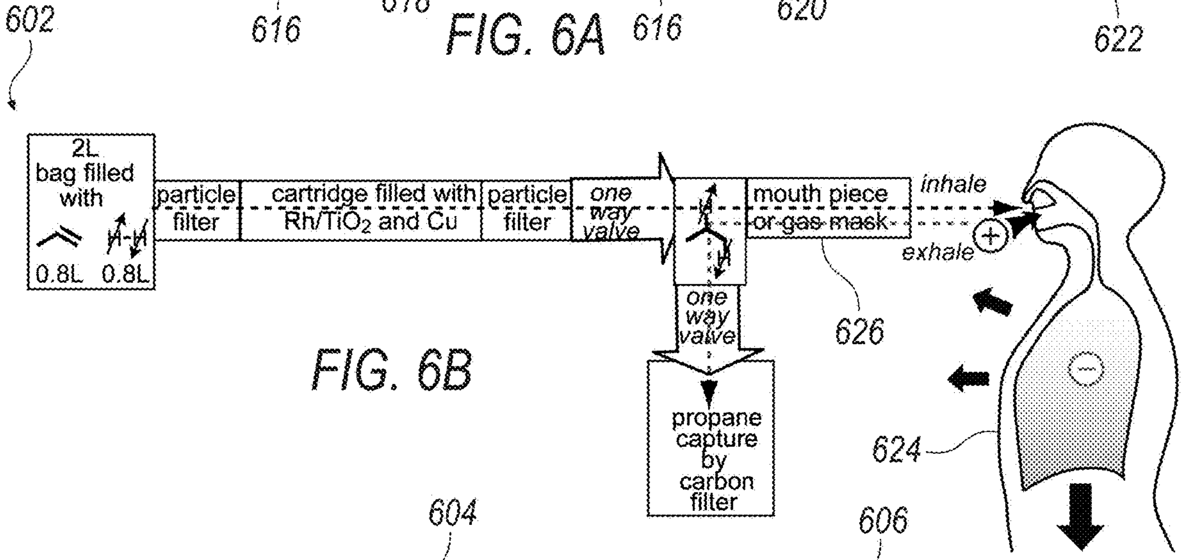
FIG. 6B illustrates an exemplary schematic of an apparatus for the creation and administration of a RASER-enhanced hyperpolarized contrast agent.
Figure 6C:
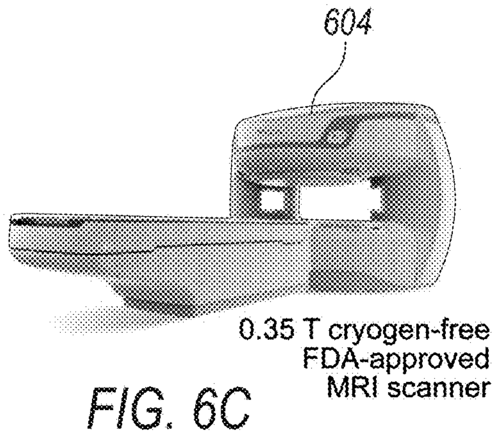
FIG. 6C illustrates an exemplary MRI device.
Figure 6D:
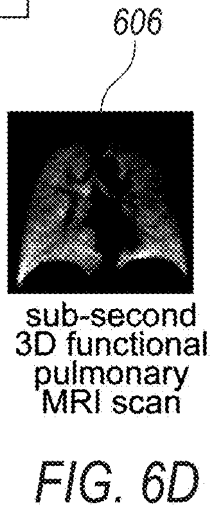
FIG. 6D illustrates an exemplary MR image.
Figure 6E:
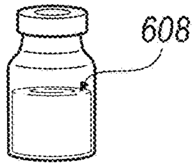
FIG. 6E illustrates an exemplary injectable RASER contrast agent.

With reference now to FIGS. 6A-6E, the following are shown: an exploded view of an exemplary apparatus 600 for the creation and administration of a RASER-enhanced hyperpolarized contrast agent (FIG. 6A); an exemplary schematic 602 illustrating an exemplary administration and components of a RASER-enhanced hyperpolarized contrast agent (FIG. 6B); an exemplary MRI device 604 (FIG. 6C); an exemplary MR image 606 (FIG. 6D), and an exemplary injectable RASER contrast agent 608 (FIG. 6E).

With reference to FIG. 6A, the exemplary apparatus 602, which may be disposable, performs HP propane polarization prior to administration of a RASER-enhanced hyperpolarized contrast agent 610 (a.k.a., a RASER inducing contrast agent). The apparatus 602 includes a bag (or other gaseous holding device) 612 filled with a gas mixture 614, two particle filters 616, a cartridge 618 that hyperpolarizes the gas mixture 612, a valve 620, and a carbon filter 622. Other examples of the apparatus may include different components in a different arrangement.

With reference to FIGS. 6A-6E, the gas mixture 614 may, for example, be a medical-grade PHIP precursor (e.g., propylene or divinyl ether) and, for example, p-$H_2$ gas that may be employed in clinical use. This exemplary pre-mixed gas 614 may have a relatively long shelf-life of, for example, approximately a week or longer since pH2 may be stable for weeks to months. It is noted other pre-mixed gases may be employed. Further, gas may be mixed via the device or in a different manner. Nonetheless, the exemplary pre-mixed gas 614 may be placed in the breathing bag 612 and, in turn, may be coupled to one of the particle filters 616.

The cartridge 616 (a.k.a. reactor) provides conversion of propylene and pH2 into HP propane or HP diethyl ether gas 610 prior to a patient 624 inhaling the exemplary converted gas 610 (i.e., the RASER inducing contrast agent). The patient 624 may, for example, perform a quick (e.g., 1-2-s long) inhalation of HP propane gas via a mouthpiece, mask, or other inhalation device 626 of the apparatus 600.

The valve 620 may be a non-rebreathing valve. As such, the patient 624 may then, for example, hold their breath (e.g., for ~2-4 seconds) and exhale the gas into the same tubing using the same mouth piece 626. The exhaled (depolarized) propane (or diethyl ether) gas may then, for example, exit through a port 628 of the apparatus 600. Further, the exhaled gas may then, for example, be captured by the carbon filter 622, ensuring that the utilized gas does not enter an MRI room, or at least minimizing its entrance. While the quantities of flammable gases employed may be small (e.g., ~1 L), the clinical MRI room may, for example, be equipped with propane and hydrogen sensors as an extra precaution to ensure safety.

The RASER inducing contrast agent 610 may be utilized to obtain MR images via an exemplary MRI device (e.g., MRI device 604). For example, during a breath-hold, a series of functional 3D MRI images (or other MR images, see exemplary image 606) may be recorded with temporal resolution of, for example, one second. The duration of the scan procedure may, for example, be less than 15 seconds from the RASER inducing contrast agent 610 production to exhalation/re-collection. Further, if desired, RF pulse activation can be avoided. That is, since the Radio amplification by RASER condition can result from the interaction between the inhaled bolus of hyperpolarized contrast agent (i.e., the RASER inducing contrast agent 608) and the radio-frequency RF coil of the exemplary MRI device (e.g., MRI device 604) resonating at the relevant Larmor frequency, proper conditions are created for obtaining MR images (e.g., the exemplary MR image 606) with or without implementation of RF pulses.

The functional pulmonary images (e.g., the exemplary image 606) may, for example, be co-registered with the anatomical images obtained on the exemplary MRI device during the same imaging session, or from a different scanner taken during a different session. The imaging session may, for example, last less than 1 minute. It is noted that, in some examples, there is no need for RF pulse calibration and static magnetic field mapping, for example for a 0.35 T MRI scanner. As such, time-consuming steps can be avoided. Further, the technique can yield minimal patient discomfort while providing a non-invasive, high-resolution MRI scan of lung function using no ionizing radiation.

In contrast to a gaseous RASER inducing contrast agent (e.g., RASER inducing contrast agent 610), an injection of hyperpolarized contrast agent (e.g., the injectable RASER inducing contrast agent 608) may be employed to record MR imaging (e.g., MR imaging as a of function and metabolism). That is, like the gaseous RASER inducing contrast agent 610 discussed above with respect to FIGS. 6A and 6B, the injectable RASER inducing contrast agent 608 may be employed in a patient (e.g., patient 614). Further, similar to the gaseous RASER inducing contrast agent 610 of FIGS. 6A and 6B, since a RASER condition can result from the interaction between the injected bolus of hyperpolarized contrast agent (i.e., the injectable RASER inducing contrast agent 608) and the radio-frequency RF coil of an exemplary MRI device resonating at the relevant Larmor frequency, proper conditions are created for obtaining MR images with or without implementation of RF pulses. Benefits of employing the injectable RASER inducing contrast agent 608 is that the injection can be made in such a manner that other organs or systems may be imaged by leveraging the induced RASER environment.

It is noted that examples do not simply employ hyperpolarized contrast agents while MR imaging occurs. Rather, a RASER state of hyperpolarized contrast is employed once the bolus of hyperpolarized contrast agent is inside the patient. That is, the stimulated emission is created spontaneously through the interaction of the parahydrogen-produced magnetization and the detector without application of RF pulses, or prior to imaging occurs. The stimulated emission provides additional signal amplification of hyperpolarized MRI providing clear sensitivity and resolution benefits. This is in contrast to other MR imaging modalities where the applications of RF pulses are generally needed to obtain MR images.

Accordingly, unlike other imaging modalities, the implementation of the RASER inducing contrast agent (e.g., gaseous or injectable) discussed herein causes the subject to become a RASER after receiving a dose of parahydrogen-hyperpolarized contrast agent, thus allowing MR imaging to occur without the application of RF pulses if desired.

In some examples, the hyperpolarization pool may be retained on spin-1/2 heteronucleus (for example, C-13, N-15, F-19 and others), which may retain a hyperpolarized state significantly longer than protons. These agents carrying heteronucleus may render RASER signals at frequencies corresponding to resonance frequencies of, for example, the C-13, N-15, F-19 and other nuclei, or the RASER signal may be re-created on protons using hyperpolarization stored on these C-13, N-15, F-19 and other nuclei. A benefit of using C-13, N-15, F-19 and other nuclei is due to the longer-lived hyperpolarized states, as their $T_1$ may be longer under physiological conditions.

Examples may be employed in a wide variety of areas such as in the context of PHIP studies and biomedical applications. The HP substrates used herein may be employed as, for example, in vivo RASER inducing contrast agents. For example, HP HEP RASER inducing contrast agent(s) may be employed in the context of, for example, angiography. Moreover, by employing PHIP via side-arm hydrogenation (SAH), the range of biomolecules (including ethyl acetate) that can be hyperpolarized via PHIP may be expanded. With this technique(s), a wide range of carboxylic acids may be hyperpolarized and employed in vivo for metabolism tracking.

The technique(s) described herein may employ, for example, a commercially available NMR spectrometer with unaltered room-temperature RF coil with Q of ~68. Further, it is noted that PHIP-RASER under both PASADENA and ALTADENA conditions show J-coupling and chemical-shift controlled dynamics of RASER signal evolution. RF stimulation is not required to induced RASER effect. Next, two exemplary molecular moieties (i.e., acetate and propionate via pairwise p-$H_2$ addition to double C═C bond) effective in, for example, in vivo bio-imaging studies of perfusion and metabolism are represented herein. Further, the process of batch hyperpolarization may be employed, for example, when a bolus of material is hyperpolarized over a short period of time (e.g., 10 s). The bolus may then be employed in, for example, in vivo imaging applications, thus paving the way to potential future use of RASER in bio-imaging applications. Accordingly, implementing RASER MRI scan(s) has the potential to revolutionize MRI and medical imaging.

RASER activity of two exemplary PHIP-hyperpolarized compounds discussed herein may arise through the use of standard NMR hardware at low concentrations (e.g., approximately 40 mM) and at estimated proton polarization values of over 10% at the time of the detection-potentially lower concentration are feasible. RASER activity is observed with and without applications of RF excitation pulses. Further, this RASER activity is observed under, for example, both ALTADENA and PASADENA conditions. J-coupling constants as well as chemical shift differences may be measured with increased precision. Technique(s) and contrast agent(s) discussed herein may be employed in, for example, studies that aim at providing highly polarized RASER inducing contrast agents for imaging of metabolism (i.e., where high levels of polarization at high substrate concentrations are desired). The parahydrogen-induced RASER phenomenon described here may enable other new applications in magnetic resonance imaging and beyond.

Figure 7:
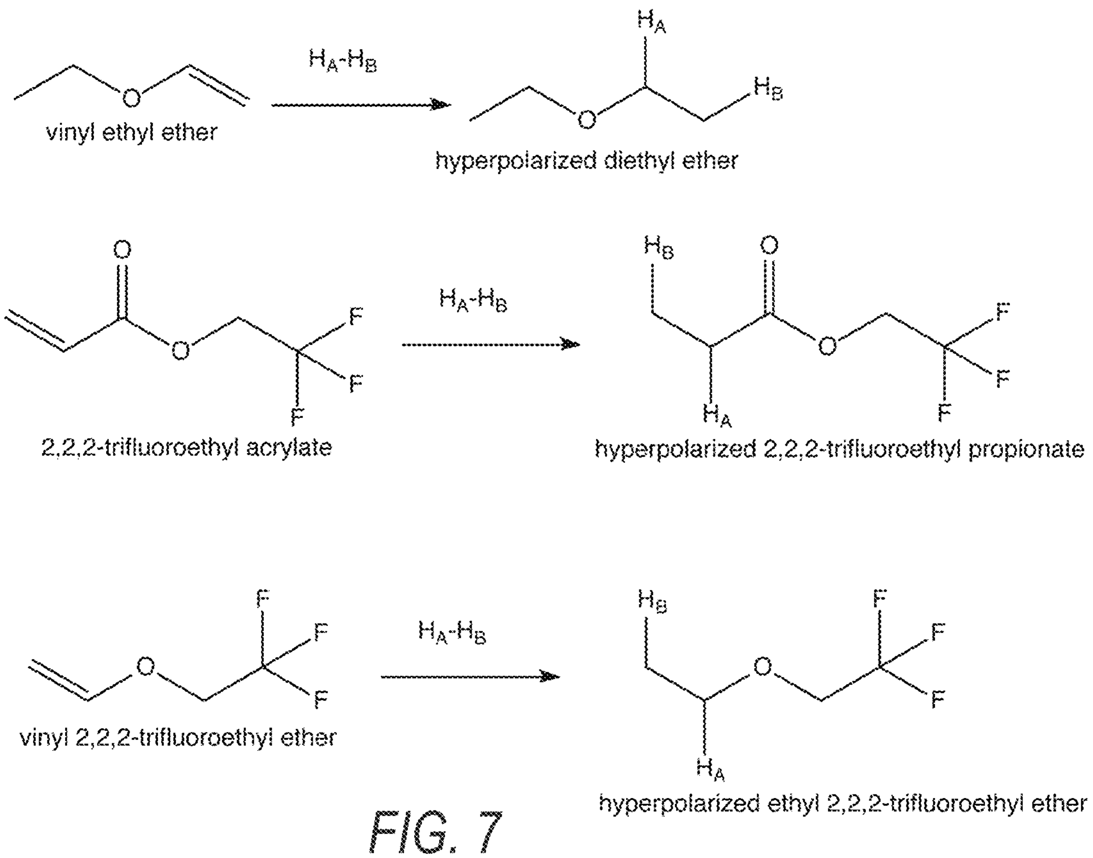
FIG. 7 illustrates an exemplary schematic of pairwise parahydrogen (p-$H_2$) addition (shown as HA-HB) to five unsaturated precursors resulting in production of proton-hyperpolarized products, which render a PHIP RASER condition.
Figure 8:
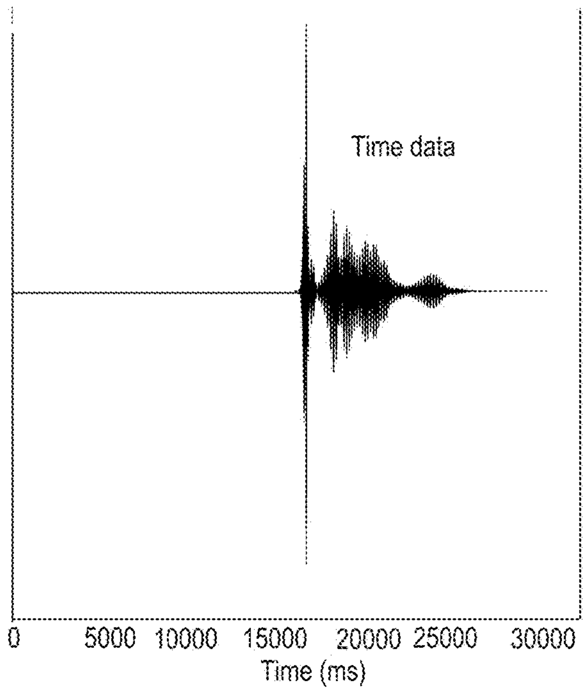
FIG. 8 illustrates an exemplary $^{1}H$ NMR spectroscopy of hyperpolarized diethyl ether (produced via hydrogenation path shown in FIG. 7) probed at 1.4 T: ALTADENA RASER signal recorded without an RF pulse after hydrogenation in the Earth's magnetic field.
Figure 9:
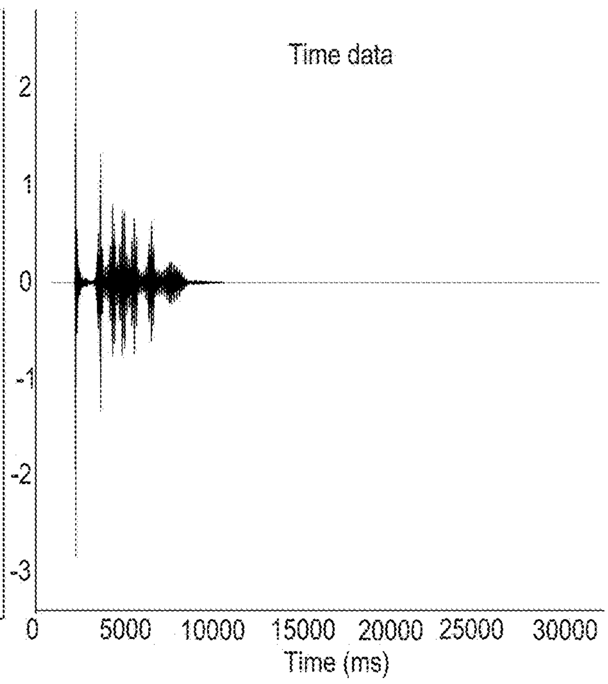
FIG. 9 illustrates an exemplary $^{1}H$ NMR spectroscopy of hyperpolarized 2,2,2-trifluoroethyl propionate (produced via hydrogenation path shown in FIG. 7) probed at 1.4 T: ALTADENA RASER signal recorded without an RF pulse after hydrogenation in the Earth's magnetic field.
Figure 10:
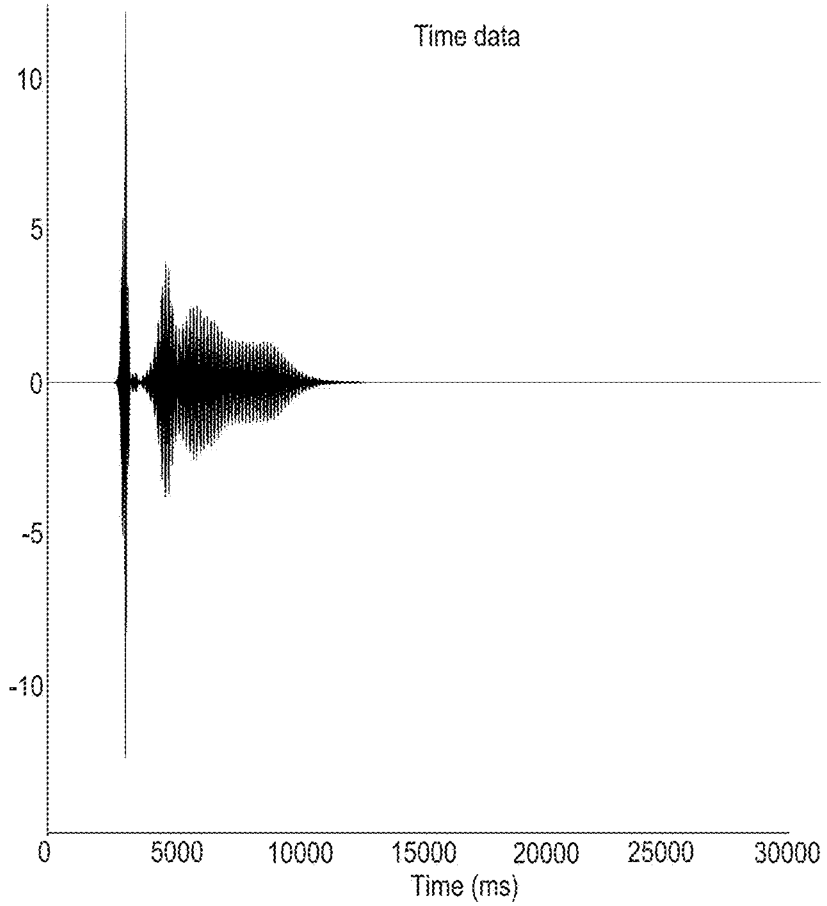
FIG. 10 illustrates an exemplary $^{1}H$ NMR spectroscopy of hyperpolarized ethyl 2,2,2-trifluoroethyl ether (produced via hydrogenation path shown in FIG. 7) probed at 1.4 T: ALTADENA RASER signal recorded without an RF pulse after hydrogenation in the Earth's magnetic field.

Besides the two compounds demonstrated in Figure set 3 and 4, RASER can be observed on a wide range of other substrates. FIG. 7 illustrates three other exemplary compounds that are hyperpolarized by parahydrogen pairwise addition and may be employed as inhalable contrast agents, including most notably hyperpolarized diethyl ether, which is relatively non-toxic. That is, non-toxic or relatively non-toxic RASER inducing contrast agents are envisioned that may be used in living subjects.

Figure 11:
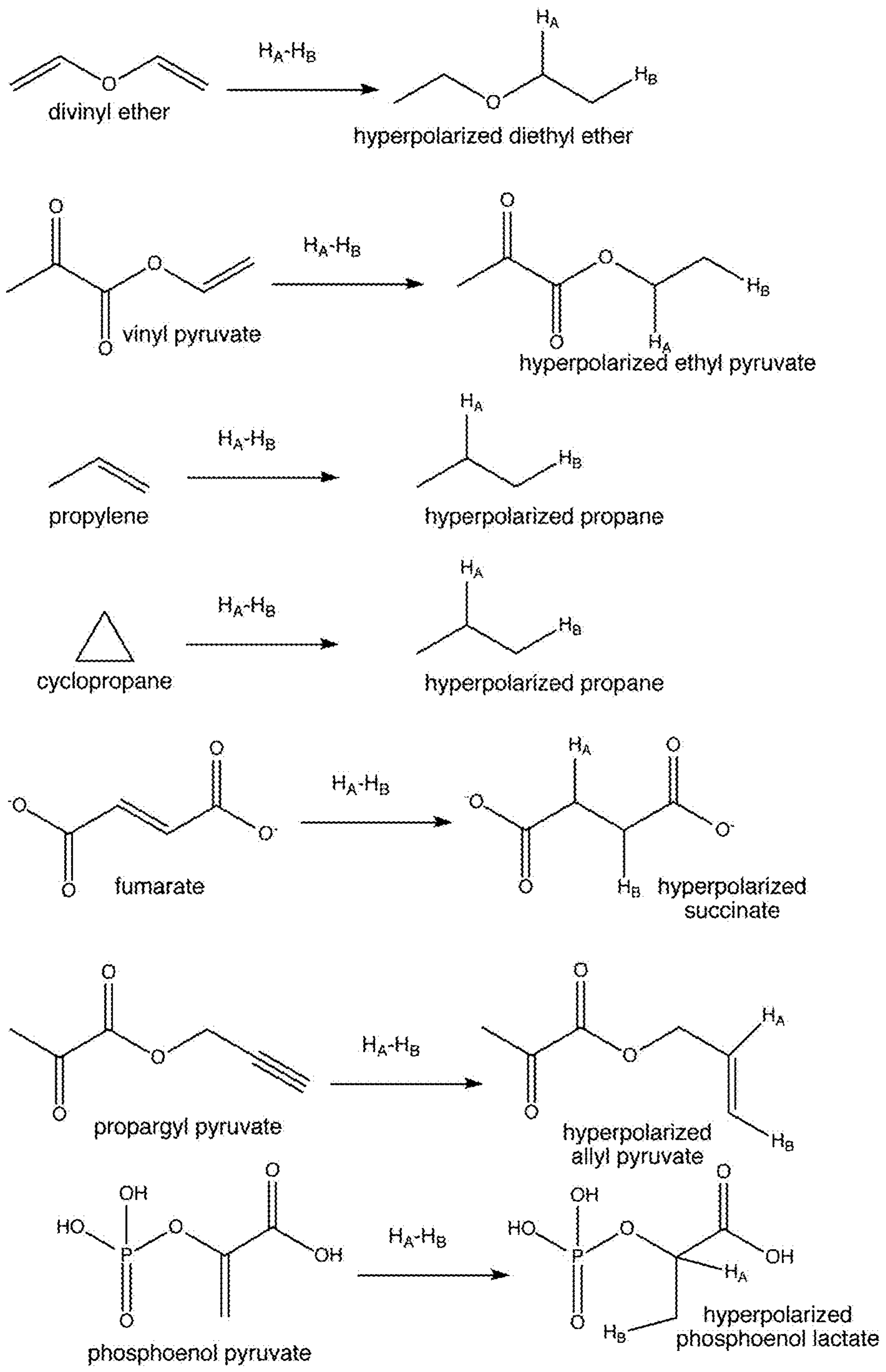
FIG. 11 illustrates an exemplary schematic of pairwise parahydrogen addition (shown as HA-HB) to seven unsaturated precursors resulting in production of hyperpolarized products, which may be amenable to render a PHIP RASER condition.

Other exemplary hyperpolarized compounds with biomedical relevance which can readily produce RASER via PHIP hyperpolarization are represented in FIG. 11.

It is noted that performing a reaction of parahydrogen addition to unsaturated molecular precursor results in generally highly concentrated and sufficiently hyperpolarized states. These states may render RASER with a conventional RF coil of MRI magnet in order to enable a new kind of MRI scan. For example, these states may enable MR imaging scans free of RF pulse excitations. Also, performing a reaction of parahydrogen addition to unsaturated molecular precursor results in highly concentrated and sufficiently hyperpolarized states in order to render RASER with MODIFIED (enhanced quality factor) RF coil of MRI magnet in order to enable another exemplary new kind of MRI scan. While in high-field MRI (e.g., 1.0 T and above), the quality factor of the loaded RF coil is generally dominated by the subject (e.g., the patient). That is, the quality factor of RF coils in low field MRI (e.g., 0.35 T and below) is no longer limited by insertion of the patient. Further, PHIP-RASER may also be created using higher-quality-factor RF coils compared to those normally supplied by the commercial vendors.

While the stimulated emission discussed herein may be triggered by the application of RF pulse(s) to enable detection of MRI signal, it need not be triggered by RF pulses.

Examples of the RASER MRI scan described herein may benefit from additional sensitivity gain created by the stimulated emission. These gains come in addition to the signal gains derived through hyperpolarization.

An exemplary RASER MRI may also benefit from enhanced $T_2$ relaxation (due to stimulated emission), which is greater than $T_2$* of the sample. These gains come in addition to the signal gains through hyperpolarization.

An exemplary RASER MRI scan may also employs the stimulated emission as a mechanism for additional signal amplification and also as a new mechanism of contrast in MRI in vivo.

Exemplary hyperpolarized MRI contrast agents discussed herein may be employed for a new kind of MRI scan to enable, for example, pulmonary, functional and metabolic imaging.

Exemplary hyperpolarized MRI contrast agents discussed herein may also be employed substantially directly after the process of parahydrogen pairwise addition through proton detection of parahydrogen-derived hyperpolarized protons.

Further, an exemplary hyperpolarized MRI contrast agent may also be employed indirectly, where parahydrogen-derived hyperpolarization is temporarily stored on heteronucleus such as $^{13}C$, $^{15}N$ or other biocompatible heteronucleus. This exemplary hyperpolarization may be detected directly in the form of a RASER signal or transferred back to $^{1}H$ sites to achieve $^{1}H$ RASER. The storage on a heteronucleus offers an advantage of a longer lived hyperpolarized state.

Exemplary implementation RASER inducement in subjects or biospecimens is not limited to low magnetic fields or the use of resonators with high quality factors. For example, a commercial, bench-top 1.4 T NMR spectrometer in conjunction with parahydrogen pairwise addition producing proton-hyperpolarized molecules in the Earth's magnetic field (a.k.a., ALTADENA) may be employed.

Further, in a high magnetic field (e.g., a PASADENA condition), RASER can be induced without any radiofrequency excitation pulses. The results demonstrate that RASER activity can be observed on a wide variety of NMR spectrometers and measures with a high precision on many NMR parameters, such as chemical shifts and J-coupling constants. These examples are important for future applications of RASER in many different fields of science and technology, in particular for the development and quality assurance of hyperpolarization techniques such as parahydrogen-induced polarization.

Exemplary RASER inducement described herein is not limited to low magnetic fields (and by extension low frequencies) or the use of resonators with high-quality factors.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A method comprising:

converting a gas, via pairwise addition of p-$H_2$ onto double carbon bonds (C═C) of the gas, into a hyper polarized (HP) gas that exhibits parahydrogen-produced magnetization with negative nuclear spin polarization;

passing the HP gas into a subject;

magnetic resonance (MR) imaging, via an MR imaging device, to induce a radio amplification by stimulated emission of radiation condition (RASER condition) in the subject via an interaction between a radio frequency (RF) detector coil operating at a Larmor frequency and the HP gas in the subject, wherein the MR imaging is carried out without employing an RF excitation pulse; and receiving MR signals induced by the RASER condition to create at least one MR image.

2. The method of claim 1 wherein converting the gas into an HP gas occurs via passing the gas through a chemical reactor.

3. The method of claim 2 further comprising capturing flammable material exhaled by the subject in a filter.

4. The method of claim 2 wherein the MR imaging device is one of a 1.4 Tesla (T) MR system and a 0.35 T MR system.

5. The method of claim 2 wherein the MR signals are induced while the RF detector coil is operating at room temperature.

* * * * *